United States Patent [19]

Hamill et al.

[11] 4,174,390

[45] Nov. 13, 1979

[54] ANTIBIOTIC A-7413 AND PROCESS FOR PREPARATION THEREOF

[75] Inventors: Robert L. Hamill, Greenwood; W. Max Stark, Indianapolis, both of Ind.

[73] Assignee: Eli Lilly and Company, Indianapolis, Ind.

[21] Appl. No.: 932,833

[22] Filed: Aug. 11, 1978

Related U.S. Application Data

[60] Continuation of Ser. No. 766,306, Feb. 7, 1977, abandoned, which is a continuation-in-part of Ser. No. 737,456, Nov. 1, 1976, abandoned, which is a division of Ser. No. 655,670, Feb. 4, 1976, abandoned.

[51] Int. Cl.$^2$ .............................................. A61K 35/00
[52] U.S. Cl. .................................... 424/117; 424/115; 435/827; 435/170
[58] Field of Search ................... 424/117, 115; 195/80

[56] References Cited

PUBLICATIONS

Miyaiui et al., J. Antibiotics 23(3), pp. 113–119, (1970).
Mizuno et al., J. Antibiotics 21(6), pp. 429–431, (1968).
Umezawa, Index of Antibiotics from Actinomycetes, University Park Press, State College, Penn., 1967, pp. 598, 634 & 654.
Derwent Abstract #59138w, Abstracting West German Pat. No. 2507—565.
Ebata et al., J. Antibiotics, 22, (10), pp. 451–456, (1969).

*Primary Examiner*—Jerome D. Goldberg
*Attorney, Agent, or Firm*—Nancy J. Harrison; Arthur R. Whale

[57] ABSTRACT

Antibiotic A-7413 complex, comprising a major microbiologically active factor A, and minor active factors B, C, and D, is produced by fermentation of Actinoplanes sp. NRRL 8122. The individual factors are isolated and separated by extraction and chromatography. The A-7413 antibiotics are antibacterial agents. The A-7413 complex and A-7413 antibiotic compounds are also useful as growth-promoting agents and in the control of dental caries and acne.

9 Claims, 7 Drawing Figures

ANTIBIOTIC A-7413 AND PROCESS FOR PREPARATION THEREOF

CROSS-REFERENCE TO RELATED APPLICATION

This is a continuation of application Ser. No. 766,306 filed Feb. 7, 1977, which is a continuation-in-part of application Ser. No. 737,456, filed Nov. 1, 1976, which in turn is a division of application Ser. No. 655,670, filed Feb. 4, 1976, each of which prior applications is now abandoned.

BACKGROUND OF THE INVENTION

There is a continuing demand for new antibiotics. Because there are many pathogenic organisms, a number of specifically-effective antibiotic agents are needed. For example, in the treatment of such serious problems as systemic streptococcal and staphylococcal infections, new effective agents are always welcome.

Dental caries and acne are wide-spread human afflictions caused by pathogenic organisms. Dental caries is a pathological process in which there is a gradual dissolution and disintegration of the enamel and dentin of teeth. If dental caries remains untreated, eventual inflammation of the dental pulp and abscesses occur. Acne is a common inflammatory disease of the skin. It is estimated that greater than 80% of adolescents suffer from acne. Although its effects can vary greatly, acne is always troublesome and is often severe in its manifestations.

In addition to demands for new antibiotics which are useful in treating diseases in humans, improved antibiotics are also needed in the veterinary field. In one important aspect, improved antibiotics are needed to promote growth in poultry and in livestock. Growth promotion is achieved, for example, by reducing disease and by increasing feed-utilization efficiency.

THE PRIOR ART

The A-7413 antibiotics are new members of the sulfur-containing thiostrepton family of antibiotics. Other members of this family include siomycin, taitomycin, thiostrepton and thiopeptin B.

SUMMARY OF THE INVENTION

This invention relates to antibiotic substances. In particular, it relates to a group of sulfur-containing antibiotic substances which are produced by culturing a hitherto undescribed strain of the organism Actinoplanes sp. NRRL 8122.

The antibiotics of this invention are arbitrarily designated herein as A-7413 antibiotics. Three individual antibiotic factors have been isolated and separated from a fermentation broth produced by the new Actinoplanes culture. These individual antibiotics are designated as A-7413 factors A, B and C. A fourth factor, which is designated as A-7413 factor D, is a very minor component. A-7413 factor D has been separated by column, thin-layer and paper chromatography.

Each of A-7413 factors A, B and C has an acid function capable of forming salts and ester derivatives. The physiologically-acceptable salts and the $C_1$-$C_4$-loweralkyl ester derivatives of A-7413 factors A, B, and C are part of this invention.

Each of A-7413 factors A, B, and C has at least one hydroxyl group capable of forming acyl ester derivatives. The $C_1$-$C_5$-acyl ester derivatives and the physiologically-acceptable salts of said ester derivatives are also part of this invention. The A-7413 factors A, B, and C are also capable of forming derivatives with thiolcarboxylic acids. The thiol-$C_2$-$C_4$-carboxylic acid derivatives of A-7413 factors A, B, and C and the physiologically-acceptable salts of these derivatives are also part of this invention.

For simplicity in discussions of utility, the term "A-7413 compound" is used herein to refer to a compound selected from the group consisting of A-7413 factors A, B, and C; the specified ester, acyl-ester, and thiolcarboxylic acid derivatives of A-7413 factors A, B, and C; and the physiologically-acceptable salts of factors A, B, and C and of the specified acyl-ester and thiolcarboxylic acid derivatives of factors A, B, and C.

The A-7413 group of antibiotics is produced by culturing a novel strain of Actinoplanes sp. NRRL 8122 under submerged aerobic fermentation conditions until a substantial level of antibiotic activity is produced. The A-7413 antibiotics are recovered as an antibiotic complex by extraction of both the broth and the mycelia with polar organic solvents.

The term "antibiotic complex" as used in the fermentation art and in this specification refers to a mixture of co-produced individual antibiotic factors. As will be recognized by those familiar with antibiotic production by fermentation, the ratio of individual factors produced in an antibiotic complex will vary, depending on the fermentation conditions used.

The individual A-7413 antibiotic factors are separated from the A-7413 complex and are isolated as individual antibiotic compounds by separation techniques such as column chromatography, thin-layer chromatography, countercurrent distribution, and crystallization procedures.

The A-7413 complex and the A-7413 compounds inhibit the growth of certain pathogenic organisms, especially the gram-positive bacteria. In addition, the A-7413 complex and the A-7413 compounds are useful in the prevention and treatment of dental caries and in the treatment of acne. Furthermore, the A-7413 complex and the A-7413 compounds are growth-promoting agents for poultry and increase feed-utilization efficiency in ruminants.

DESCRIPTION OF THE DRAWINGS

The infrared absorption spectra of individual A-7413 factors A, B, and C in KBr disc are presented in the drawings as follows.

DETAILED DESCRIPTION OF THE INVENTION

The A-7413 complex comprising factors A, B, C, and D is produced by cultivating under controlled conditions a hitherto undescribed strain of Actinoplanes sp. NRRl 8122.

As is the case with many antibiotic-producing cultures, fermentation of an A-7413-producing strain of Actinoplanes sp. NRRL 8122 results in the production of a number of antibiotic substances. Antibiotic A-7413 factor A is the major factor produces by this culture, and factors B, C, and D are three minor factors. Other factors are present in only very minor quantities or are relatively unstable.

The antibiotic factors A, B, C, and D are coproduced during the fermentation and are obtained as a mixture, the A-7413 complex. The individual antibiotic factors are separated from each other and isolated as individual compounds as hereinafter described.

A-7413 FACTOR A

A-7413 factor A is a white to light-yellow crystalline material which melts with decomposition at about 205–212° C. A-7413 factor A crystallizes from ethanol, chloroform:ethanol, and dimethylformamide:acetone.

A-7413 factor A is soluble in methanol, chloroform, dimethylformamide, dichloroethane and dimethyl sulfoxide (DMSO); is slightly soluble in ethanol and aqueous ethanol; but is insoluble in acetone, benzene, carbon tetrachloride, dichloromethane, methyl isobutyl ketone, ethyl acetate, diethyl ether and water.

Elemental analysis of A-7413 factor A indicates the following approximate percentage composition (average): carbon, 51.92%, hydrogen, 5.25%; nitrogen, 9.85%; oxygen, 22.63%; and sulfur, 9.66%. An approximate empirical formula proposed for A-7413 factor A is $C_{72}H_{87}N_{12}O_{23}S_5$.

The apparent molecular weight of A-7413 factor A is approximately 1308, as determined by titration.

Figure 1:
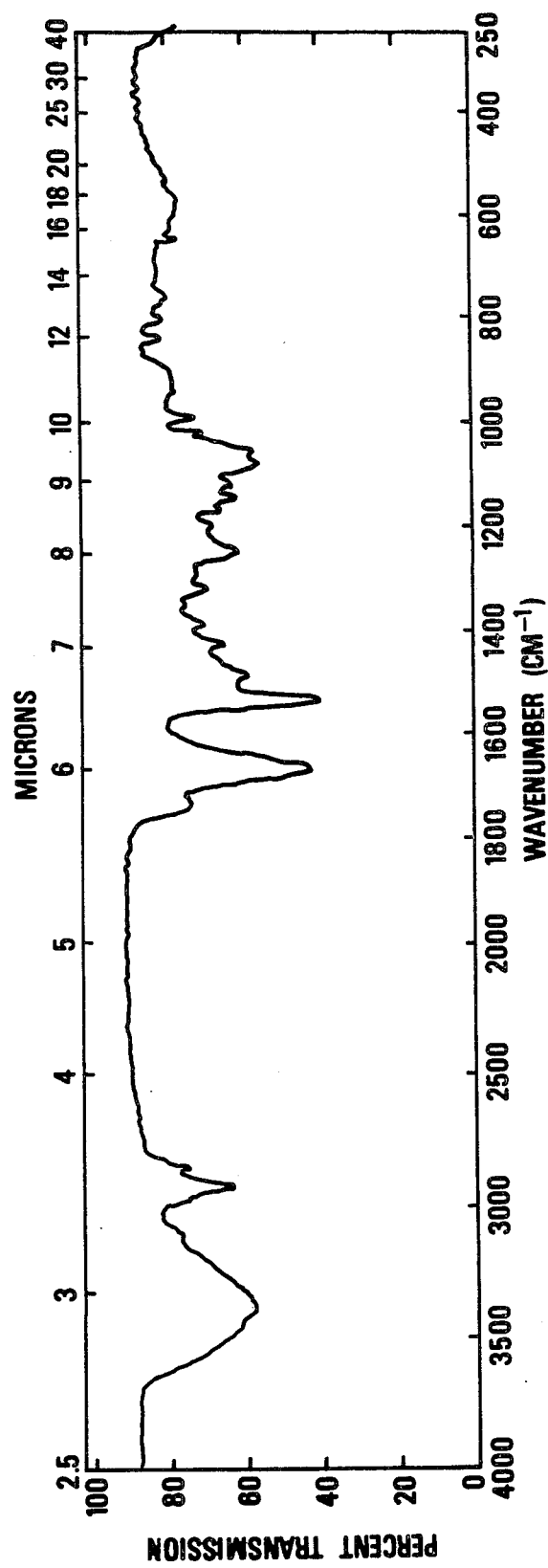
FIG. 1—A-7413 Factor A
 FIG. 2—A-7413 Factor B
 FIG. 3—A-7413 Factor C
 FIG. 4—A-7413 Factor A Methyl Ester
 FIG. 5—A-7413 Factor A Acetyl Ester Derivative
 FIG. 6—A-7413 Factor A Triacetyl Ester Derivative
 FIG. 7—A-7413 Factor A Bis(Mercaptoacetic Acid)-Derivative

The infrared absorption spectrum of A-7413 factor A in KBr disc is shown in FIG. 1 of the accompanying drawings. The following absorption maxima are observed: 2.93 (shoulder), 2.98 (medium), 3.24 (weak), 3.38 (shoulder), 3.44 (medium), 3.53 (weak), 5.78 (weak), 6.03 (strong), 6.56 (strong), 6.79 (medium), 7.08 (medium), 7.27 (weak), 7.49 (weak), 7.65 (weak), 8.08 (medium), 8.41 (weak), 8.62 (weak), 8.81 (medium), 9.03 (weak), 9.35 (medium, 9.60 (medium), 9.92 (weak), 10.20 (weak), 12.05 (weak), 12.66 (weak), and 13.51 (weak) microns.

The ultraviolet absorption spectrum of A-7413 factor A exhibits the following absorption maxima:
(a) in neutral, 95% aqueous ethanol:
 215 nm ($E_{1cm}^{1\%}=485$);
 260 nm (shoulder; $E_{1cm}^{1\%}=240$);
 300 nm (shoulder; $E_{1cm}^{1\%}=170$);
 358 nm (shoulder; $E_{1cm}^{1\%}=112.5$);
(b) in acidic ethanol:
 217 nm ($E_{1cm}^{1\%}=440$);
 265 nm ($E_{1cm}^{1\%}=227.5$);
 293 nm ($E_{1cm}^{1\%}=210$);
 358 nm ($E_{1cm}^{1\%}=95$);
(c) in basic methanol:
 278 nm (shoulder; $E_{1cm}^{1\%}=255$);
 408 nm ($E_{1cm}^{1\%}=80$).

Electrometric titration of A-7413 factor A in 80% aqueous dimethylformamide indicates the presence of a titratable group with a $pK_a$ value of 7.9.

Amino-acid analysis of A-7413 factor A, after acidic hydrolysis, indicates the presence of ammonia (1.03μ moles/mg), glycine (0.33μ moles/mg), threonine (0.40μ moles/mg), aspartic acid (0.1μ moles/mg), and an as-yet-unidentified amino acid (approx. 0.4μ moles/mg).

A-7413 factor A has a specific rotation, $[\alpha]_D^{25}$, of +54.5° (c 2.0, $CHCl_3$).

A-7413 factor A, crystallized from chloroform:ethanol, has the following characteristic X-ray powder diffraction pattern ($Cu^{++}$ radiation, 1.5405 λ, nickel filter, d=interplanar spacing in angstroms):

| d | Relative Intensity |
|---|---|
| 12.44 | 100 |
| 10.77 | 70 |
| 7.96 | 100 |
| 5.71 | 50 |
| 5.09 | 80 |
| 4.53 | 100 |
| 4.25 | 80 |
| 3.88 | 80 |
| 3.61 | 10 |
| 3.44 | 10 |
| 3.03 | 5 |

A-7413 FACTOR B

A-7413 factor B is a white to light-yellow amorphous material which melts above 300° C.

A-7413 factor B is soluble in methanol, chloroform, dimethylformamide, dichloroethane and dimethyl sulfoxide; is slightly soluble in ethanol and aqueous ethanol; but is insoluble in acetone, benzene, carbon tetrachloride, dichloromethane, methyl isobutyl ketone, ethyl acetate, diethyl ether and water.

Elemental analysis of A-7413 factor B indicates the following approximate percentage composition: carbon, 66.34%; hydrogen, 8.73%; nitrogen, 2.98%; oxygen, 19.39%; and sulfur, 2.83%.

Figure 2:
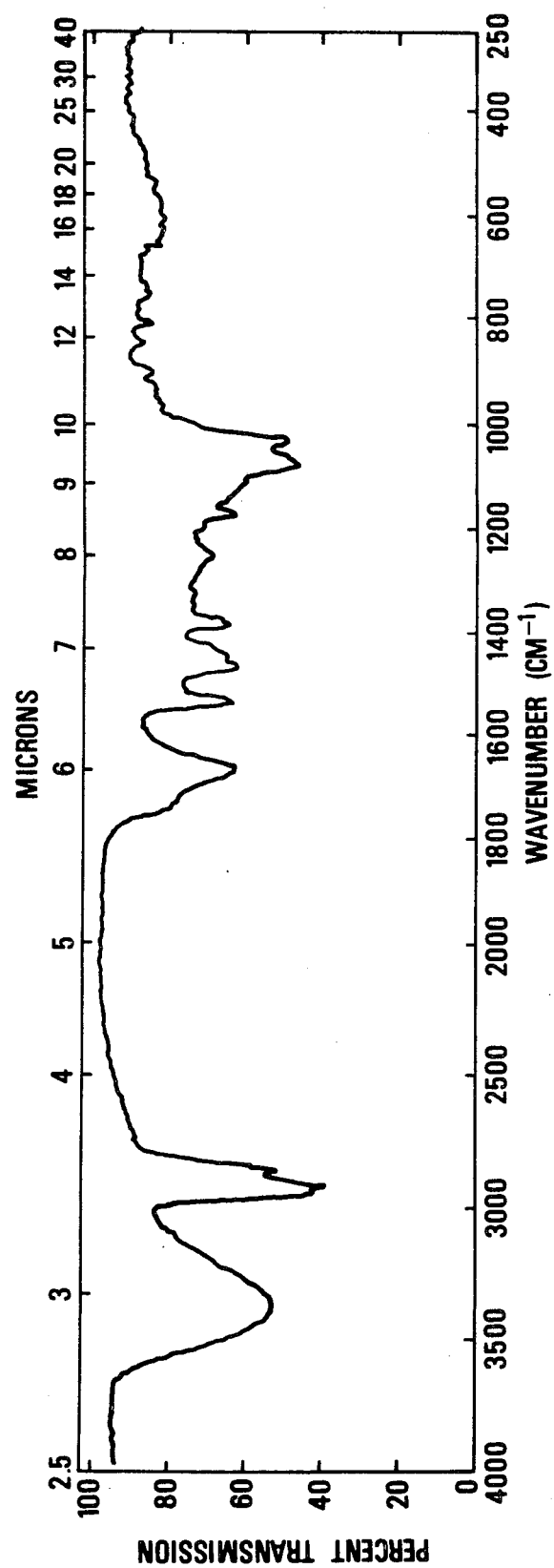

The infrared absorption spectrum of A-7413 factor B in KBr disc is shown in FIG. 2 of the accompanying drawings. The following absorption maxima are observed: 2.97 (strong), 3.38 (strong), 3.42 (strong), 3.50 (strong), 5.78 (shoulder), 5.99 (medium), 6.50 (medium), 6.80 (medium), 6.90 (shoulder), 7.00 (shoulder), 7.22 (medium), 7.27 (shoulder), 7.42 (weak), 7.58 (weak), 7.78 (shoulder), 7.97 (medium), 8.33 (shoulder), 8.53 (medium), 9.00 (shoulder), 9.26 (strong), 9.71 (strong), 11.11 (weak), 11.79 (weak), 12.35 (weak) and 13.25 (weak) microns.

The ultraviolet absorption spectrum of A-7413 factor B shows the following absorption maxima:
(a) in neutral, 95% aqueous ethanol:
 268 nm ($E_{1cm}^{1\%}=104.3$);
 357 nm (shoulder; $E_{1cm}^{1\%}=30$);
(b) in acidic ethanol:
 268 nm ($E_{1cm}^{1\%}=108.5$);
 357 nm (shoulder; $E_{1cm}^{1\%}=35$);
(c) in basic ethanol:
 268 nm (shoulder; $E_{1cm}^{1\%}=178.6$).

A-7413 factor B has a specific rotation, $[\alpha]_D^{RT}$, of −26.2° (c 7.5, DMSO).

Amino-acid analysis of A-7413 factor B, after acidic hydrolysis, indicates the presence of ammonia (0.46μ moles/mg), glycine (0.1μ moles/mg), threonine (0.1μ moles/mg), aspartic acid (0.02μ moles/mg), and an asyet-unidentified amino acid (approx. 0.11μ moles/mg).

A-7413 FACTOR C

A-7413 factor C is a white to light-yellow amorphous material which melts about 250° C.

A-7413 factor C is soluble in methanol, chloroform, dimethylformamide, dichloroethane and dimethyl sulfoxide; is slightly soluble in ethanol and aqueous ethanol; but is insoluble in acetone, benzene, carbon tetrachloride, dichloromethane, methyl isobutyl ketone, ethyl acetate, diethyl ether and water.

Elemental analysis of A-7413 factor C indicates the following approximate percentage composition: carbon, 69.38%; hydrogen, 9.92%; nitrogen, 2.34%; oxygen, 16.58%; and sulfur, 1.73%.

Figure 3:
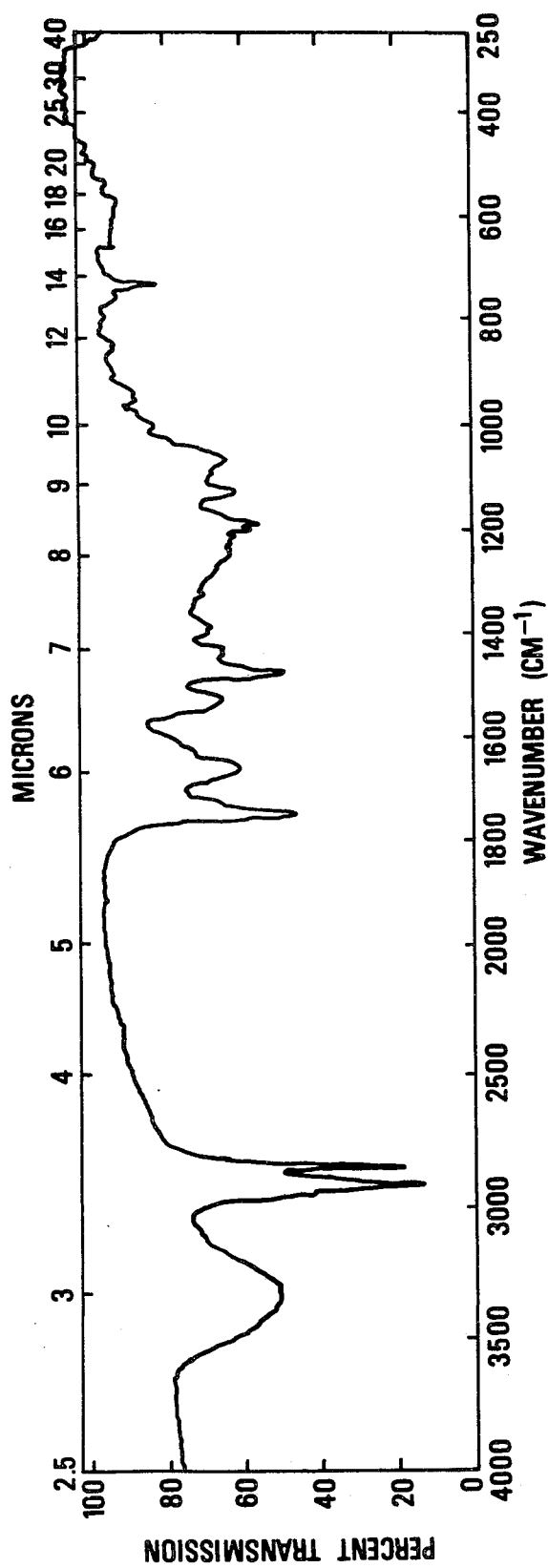

The infrared absorption spectrum of A-7413 factor C in KBr disc is shown in FIG. 3 of the accompanying drawings. The following absorption maxima are observed: 3.00 (medium), 3.38 (shoulder), 3.42 (strong), 3.51 (strong), 5.73 (medium), 6.02 (medium), 6.14 (shoulder), 6.52 (weak), 6.56 (weak), 6.77 (medium), 6.80 (shoulder), 6.97 (weak), 7.20 (weak), 8.25 (weak), 8.33 (weak), 8.40 (weak), 8.86 (weak), 9.39 (weak), 10.05 (weak), 10.53 (weak), 10.70 (weak), 11.77 (weak) and 13.66 (weak) microns.

Amino-acid analysis of A-7413 factor C, after acidic hydrolysis, indicates the presence of ammonia (0.24$\mu$ moles/mg), glycine (0.05$\mu$moles/mg), threonine (0.04$\mu$ moles/mg), aspartic acid (0.01$\mu$ moles/mg), and phenylalanine (0.05$\mu$ moles/mg).

The ultraviolet absorption spectrum of A-7413 factor C shows the following absorption maxima:
(a) in neutral, 95% aqueous ethanol:
  205 nm ($E_{1cm}^{1\%} = 356$);
  235 nm ($E_{1cm}^{1\%} = 180$);
  260 nm (shoulder; $E_{1cm}^{1\%} = 127$);
  290 nm (shoulder; $E_{1cm}^{1\%} = 104$);
(b) in acidic ethanol;
  205 nm ($E_{1cm}^{1\%} = 356$);
  235 nm (shoulder; $E_{1cm}^{1\%} = 180$);
  260 nm (shoulder; $E_{1cm}^{1\%} = 127$);
  290 nm (shoulder; $E_{1cm}^{1\%} = 103$);
  355 nm (shoulder; $E_{1cm}^{1\%} = 40$);
(c) in basic ethanol:
  260 nm (shoulder; $E_{1cm}^{1\%} = 268$);
  325 nm (shoulder; $E_{1cm}^{1\%} = 189$).

The $R_f$ values of A-7413 factors A, B, C, and D in various paper-chromatographic systems, using *Bacillus subtilis* ATCC 6633 as a detection organism, are given in Table I:

TABLE I

| Solvent System | $R_f$ Values | | | |
| --- | --- | --- | --- | --- |
|  | A7413-A | A7413-B | A7413-C | A7413-D |
| Butanol sat. with water | 0.57 | 0.46 | 0.82 | 0.61 |
| Methyl isobutyl ketone: butanol: water (25:21:4) | 0.49 | 0.33 | 0.90 | 0.61 |
| Methanol:water (1:1) | 0.62 | 0.58 | 0.31 | 0.62 |
| Water:methanol: acetone (12:3:1); adjusted to pH 10.5 with NH$_4$OH and then lowered to pH 7.5 with H$_3$PO$_4$ | 0.30 | 0.26 | 0.06 | 0.20 |
| Methanol:0.1 N HCl (3:1) | 0.71 | 0.71 | 0.42 | 0.71 |

The $R_f$ values of A-7413 factors A, B, C, and D in two thin-layer chromatographic systems of silica gel (precoated plates, E. Merck, Darmstadt, F-254, layer thickness 0.25 nm), again using *B. subtilis* ATCC 6633 as a detection organism, are listed in Table II:

TABLE II

| Solvent System | A7413-A | A7413-B | A7413-C | A7413-D |
| --- | --- | --- | --- | --- |
| Chloroform: methanol (9:1) | 0.26 | 0.09 | 0.46 | 0.55 |
| Acetonitrile: water (9:1) | 0.23 | 0.03 | 0.42 | 0.48 |

A-7413 factors, A, B, and C, and the $C_1$-$C_5$-acyl-ester and thiol-$C_2$-$C_4$-carboxylic-acid derivatives thereof are capable of forming salts. The physiologically-acceptable alkali-metal, alkaline-earth-metal and amine salts of A-7413 factors A, B, and C; of the $C_1$-$C_5$-acyl-ester derivatives of A-7413 factors A, B, and C; and of the thiol-$C_2$-$C_4$-carboxylic-acid derivatives of A-7413 factors A, B, C are also part of this invention. "Physiologically-acceptable" salts are salts which are also pharmaceutically acceptable, that is, salts in which the toxicity of the compound as a whole is not increased relative to the non-salt form. Representative and suitable alkali-metal and alkaline-earth-metal salts include the sodium, potassium, lithium, cesium, rubidium, barium, calcium, and magnesium. Suitable amine salts include the ammonium; the primary, secondary, and tertiary $C_1$-$C_4$-alkylammonium; and hydroxy-$C_2$-$C_4$-alkylammonium salts. Illustrative amine salts include those formed by reaction with ammonium hydroxide, sec-butylamine, isopropylamine, diethylamine, di-isopropylamine, ethanolamine, triethylamine, and the like.

The alkali-metal and alkaline-earth-metal cationic salts are prepared according to procedures commonly employed for the preparation of cationic salts. For example, the free acid form of A-7413 factor A is dissolved in a suitable solvent, such as methanol or ethanol; to this solution is added a solution containing the stoichiometric quantity of the desired inorganic base. The salt thus formed can be isolated by routine methods, such as filtration or evaporation of the solvent.

The salts formed with organic amines can be prepared in a similar manner. For example, the amine can be added to a solution of A-7413 factor A in a suitable solvent such as methanol; and the solvent and excess amine can be removed by evaporation.

The $C_1$-$C_4$-lower-alkyl ester derivatives of A-7413 factors A, B, and C are also part of this invention. These ester derivatives are prepared by conventional means.

As will be appreciated by those skilled in the art, many of the characteristics of the parent factors, such as ultraviolet absorption, amino-acid content and solubility are unchanged by ester formation. Other of the ester-derivative characteristics, such as infrared spectrum, molecular weight and elemental composition will differ from the parent factor only slightly and in a predictable manner.

A-7413 factors A, B, and C are capable of forming acyl-ester derivatives. The $C_1$-$C_5$-acyl-ester derivatives of A-7413 factors A, B, and C are prepared by standard techniques. For example, A-7413 factor A free acid, in a suitable solvent, is reacted with the appropriate acid anhydride for a suitable length of time to give the desired A-7413 factor A acyl-ester derivative.

Again, as those in the art will appreciate, many of the characteristics of the parent factors, such as ultraviolet absorption, electrometric titration, amino-acid content and solubility are not changed by acyl-ester formation. Other of the acyl-ester derivative characteristics, such as infrared spectrum, molecular weight, and elemental composition will differ from the parent factor only slightly and in a predictable manner.

A-7413 factors A, B, and C are also capable of forming derivatives with thiolcarboxylic acids. These derivatives are prepared according to the method of M. Ebata et al., *J. Antibiotics* 22 (10), 451–456 (1969). Although the character of these derivatives is not known, the derivatives retain at least one carboxyl group and are able to form salts. The thiol-$C_2$-$C_4$-carboxylic acid derivatives of A-7413 factors A, B, and C which are a part of this invention include, for example, the derivatives prepared from mercaptoacetic acid (thioglycolic acid), 2-mercaptopropionic acid (thiolactic acid), 3-mercaptopropionic acid, mercaptosuccinic acid (thiomalic acid), and L-cysteine.

The newly-found and hitherto undescribed microorganism which produces the A-7413 antibiotic complex has been characterized taxonomically as a species of the Actinoplanes genus.

The genus Actinoplanes is a member of the family Actinoplanaceae. The Actinoplanaceae are a family of microorganisms of the order Actinomycetales, having been first described by Couch [*J. Elisha Mitchell Sci. Soc.*, 65, 315–318 (1949); 66, 87–92 (1950); *Trans. New York Acad. Sci.*, 16, 315–318 (1954); *J. Elisha Mitchell Sci. Soc.*, 71, 148–155 and 269 (1955); "Bergey's Manual of Determinative Bacteriology," 8th Edition, 706–711 (1974); *J. Elisha Mitchell Sci. Soc.*, 79, 53–70 (1963)].

A culture of the A-7413-producing microorganism has been deposited with the permanent culture collection of the Northern Regional Research Laboratory, Agricultural Research Service, U.S. Department of Agriculture, Peoria, Illinois 61604, where it has been accorded the accession number NRRL 8122.

The characteristics of Actinoplanes sp. NRRL 8122 are given in the following paragraphs. The methods recommended for the International Streptomyces Project [E. B. Shirling and D. Gottleib, *Intern. Bull. Systematic Bacteriol.* 16, 313–340 (1966)] for the characterization of Streptomyces species have been used along with certain supplementary tests. Color names were assigned according to the I.S.C.C.-N.B.S. method [K. L. Kelly and D. B. Judd, "The ISCC-NBS Method of Designating Colors and a Dictionary of Color Names," U.S. Dept. of Commerce Circular No. 553, Washington, D.C.]. The Maerz and Paul color blocks (A. Maerz and M. R. Paul, "Dictionary of Color," McGraw-Hill Book Company, New York, N.Y., 1950) are enclosed in parenthesis.

MORPHOLOGY

Vegetative mycelia and sporangia are extensively produced on sweetgum (Liquidambar) pollen. There is no evidence of hyphae penetrating the pollen. No sporangia are produced on Pinus pollen.

Sporangia are usually 9$\mu$ to 14$\mu$ in diameter, varying in shape from globose to subglobose to irregular. The principal shape is irregular. Spores are spherical, multi-flagellated, 1.4$\mu$ to 1.7$\mu$; only a few become motile.

| CULTURAL CHARACTERISTICS (after 21 days at 30° C.) | |
|---|---|
| Yeast-malt (ICP No. 2) | Growth abundant, light brown (12I8); no soluble pigment; sporangia are produced. |
| Czapek's agar | Growth abundant, moderate orange (11J8); no soluble pigment; no sporangia are produced. |
| Oatmeal agar (ICP No. 3) | Growth fair, pale yellow green (10B1); no soluble pigment; sporangia are produced. |
| Inorganic salts-starch (ICP No. 4) | Growth moderate, brownish orange (13A10); slight brownish soluble pigment; sporangia are produced. |
| Glycerol-asparagine (ICP No. 5) | Growth abundant, medium reddish orange (10A10); no soluble pigment; sporangia are produced. |
| Bennett's medium | Growth fair, pale yellow (11C1); neither soluble pigment nor sporangia are produced. |
| Tomato paste-oatmeal | Growth sparse; neither soluble pigment nor sporangia are produced. |
| Tyrosine agar | Growth fair, yellowish gray (12A2); neither sporangia nor soluble pigment is produced. |
| Yeast extract agar | Growth abundant, brownish orange (13B9); neither soluble pigment nor sporangia are produced. |
| Glucose-asparagine | Growth moderate, pale orange yellow (11A4); neither soluble pigment nor sporangia are produced. |
| Calcium malate | Growth moderate, light yellowish pink (10A2); neither sporangia nor soluble pigment is produced. |
| Nutrient agar | Growth sparse; neither soluble pigment nor aerial hyphae are produced. |
| Emerson's agar | Growth fair, light brown (13F8); slight reddish brown pigment; no sporangia are produced. |
| Action on skim milk | No growth. |
| Nitrate reduction | Positive. |
| Gelatin liquefaction | None after 21 days. |
| Melanin production on peptone-iron agar (ICP No. 6) | Positive. |
| Temperature requirements on glycerol-asparagine agar | Good growth from 26° to 37° C. Reddish orange color most intense at 26° C. No growth at 43° C. |

| Carbon utilization | |
|---|---|
| Rhamnose | (+) |
| Cellobiose | (−) |
| i-Inositol | (−) |
| Cellulose | − |
| Melezitose | − |
| Fructose | (+) |
| Dextrose | (+) |
| D-Xylose | (+) |
| D-Mannitol | (+) |
| Raffinose | − |
| Sucrose | + |
| Maltose | (−) |
| L-Arabinose | (−) |
| Lactose | (+) |
| Minus Carbon | − |

Utilization Code:
+ = utilization
(+) = probable util.
(−) = doubtful util.
− = no utilization As is the case with other organisms, the characteristics of the A-7413-producing culture, Actinoplanes sp. NRRL 8122, are subject to variation. For example, artificial variants and mutants of the NRRL 8122 strain may be obtained by treatment with various known mutagens such as ultraviolet rays, X-rays, high-frequency waves, radioactive rays and chemicals. All natural and artificial variants and mutants which belong to this Actinoplanes species and produce the A-7413 antibiotics may be used in this invention. These variants and mutants will have essentially the same identifying characteristics as Actinoplanes sp. NRRL 8122.

The culture medium employed to grow Actinoplanes sp. NRRL 8122 can be any one of a number of media. For economy in production, optimal antibiotic yield, and ease of product isolation, however, certain culture media are preferred. Thus, for example, a preferred carbohydrate source in large-scale fermentation is dextrin, although glucose, fructose, maltose, sucrose and the like can also be used. Although not essential for growth, an oil such as corn oil improves antibiotic production. Other useful sources of carbon include peanut oil, soybean oil, fish oil, and the like. A preferred nitrogen source is soybean flour, although soybean grits, peptones, oatmeal, peanut meal, soybean meal, cottonseed meal, amino acids and the like are also useful. Among the inorganic salts which can be incorporated in the culture media are the customary soluble salts capable of yielding sodium, potassium, iron, zinc, cobalt, magnesium, calcium, ammonium, chloride, carbonate, sulfate, nitrate, and like ions.

Essential trace elements necessary for the growth and development of the organism should also be included in the culture medium. Such trace elements commonly occur as impurities in other constituents of the medium in amounts sufficient to meet the growth requirements of the organism.

It may be necessary to add small amounts (i.e. 0.2 ml/l.) of an antifoam agent such as polypropylene glycol to large-scale fermentation media if foaming becomes a problem.

For production of substantial quantities of the A-7413 antibiotics, submerged aerobic fermentation in tanks is preferred. Small quantities of the A-7413 antibiotics may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The medium used for the growth of the vegetative inoculum can be the same as that employed for larger fermentations, but other media can also be employed.

The A-7413-producing organism can be grown at temperatures between about 20° and about 37° C. Optimum A-7413 production appears to occur at temperatures of about 25°–30° C.

As is the customary procedure in aerobic submerged culture processes, sterile air is blown through the culture medium. For efficient growth of the organism, the volume of air employed in the tank production is preferably sufficient to maintain a dissolved oxygen saturation of greater than 20 percent.

The initial pH of the uninoculated culture medium varies with the medium used. In general, the pH should be in the range of 6.5–7.5. At the end of the fermentation, the harvest pH is usually slightly lower, in the range of 6.0–7.0.

During the fermentation, antibiotic production can be followed by testing samples of the broth or of extracts of the mycelial solids for antibiotic activity. Organisms known to be sensitive to the A-7413 antibiotics are useful for this purpose. One especially useful assay organism is *Bacillus subtilis* ATCC 6633. The bioassay is conveniently performed by paper-disc assay on agar plates.

Generally, antibiotic activity is detectable on the second day of the fermentation. Maximum production of antibiotic activity usually occurs between about the third and the tenth days.

Following their production under submerged aerobic fermentation conditions, the A-7413 antibiotics previously described can be recovered from the fermentation medium by methods used in the fermentation art. The antibiotics produced during fermentation of the A-7413-producing organism are found mainly in the mycelial mass. A preferred method of recovering the A-7413 antibiotics is, therefore, by extraction of the separated mycelia. Extraction of the mycelial mass is best accomplished with methanol, but other lower alcohols and chloroform are also suitable. The A-7413 antibiotics are recovered from the extracting solvent by routine procedures to give a mixture of the A-7413 antibiotics, the A-7413 complex.

The A-7413 complex may be further purified, and the individual A-7413 factors may be separated by a variety of recognized methods such as, for example, extraction and adsorption procedures. Adsorptive materials such as alumina, silica gel, ion exchange resin, cellulose, Sephadex, and the like can be advantageously used. For example, preparative-thin-layer chromatography over silica gel, using a chloroform:methanol (9:1) solvent system can be used to separate factors A, B, C, and D, recovering each factor by elution with methanol. For large-scale separation of factors, column chromatography is preferred. In such column separations, a preferred absorbent is silica gel, and a preferred solvent system is chloroform:methanol (19:1). Factor A, the major factor, is readily separated using this method. Purification of minor factors B, C, and D, however, requires subsequent column separations of enriched fractions. Again, silica gel is a preferred adsorbent, and chloroform:methanol (19:1) is a preferred solvent system.

The A-7413 compounds are antimicrobial agents and are especially active against gram-positive microorganisms. Using the standard disc-plate screening procedure, A-7413 factors A, B, and C were tested for antimicrobial activity at 1 mg/ml on 6.35-mm discs. The results of these tests, given as the diameter in millimeters of the observed zones of inhibition, are summarized in Table III.

TABLE III

| Test Organism | A-7413 Factor A | A-7413 Factor B | A-7413 Factor C |
|---|---|---|---|
| *Staphylococcus aureus* | 23 | 20 | 14 |
| *Bacillus subtilis* | 21 | 18 | 16 |
| *Sarcina lutea* | 22 | 19 | 16 |

Furthermore, A-7413 factor A, when given by subcutaneous injection to mice, has in vivo antimicrobial activity. Two doses of A-7413 factor A were administered to mice in illustrative infections. The protection afforded is measured as an $ED_{50}$ value [effective dose to protect 50 percent of the test animals; see Warren Wick et al., *J. Baceteriol.* 81, 233–235 (1961)]. The $ED_{50}$ values for A-7413 factor A against these infections are given in Table IV:

TABLE IV

|  | ED$_{50}$* (mg/kg × 2) | Challenge LD$_{50}$ |
|---|---|---|
| *Streptococcus pyogenes* | 0.42 | 161 |
| *Diplococcus pneumoniae* | 0.39 | 387 |
| *Staphylococcus aureus* | 31.00 | 4,000 |

*Therapy at one and five hours post-infection.

A special advantage of the A-7413 compounds is their ability to inhibit organisms which are resistant to other antibiotics. In Table V are summarized the results of standard agar-dilution tests (using the ICS method) wherein A-7413 factor A was tested against a variety of *Staphylococcus aureus* strains. Results are given as the minimal inhibitory concentration (MIC) at which inhibition of the *S. aureus* strain occurred. The results obtained with the known antibiotic vancomycin in the same test are included for comparison.

TABLE V

| | MIC (mcg/ml) | |
|---|---|---|
| S. aureus Strain | A-7413 factor A | Vancomycin |
| 3055* | 0.125 | 1.0 |
| 3123* | 0.125 | 1.0 |
| H290* | 0.125 | 1.0 |
| 3074** | 0.125 | 1.0 |
| H43** | 0.125 | 1.0 |
| H114** | 0.125 | 1.0 |
| H541** | 0.062 | 1.0 |
| 3125*** | 0.125 | 1.0 |
| 3130*** | 0.062 | 1.0 |
| 3131*** | 0.062 | 1.0 |
| 3132*** | 0.062 | 1.0 |
| 3133*** | 0.062 | 1.0 |
| 3134*** | 0.062 | 1.0 |
| 3135*** | 0.062 | 0.5 |
| 3136*** | 0.125 | 0.5 |
| 3137*** | 0.125 | 1.0 |
| 3138*** | 0.062 | 1.0 |
| 3139*** | 0.125 | 1.0 |
| 3140*** | 0.125 | 0.5 |

Penicillin G susceptible
**Penicillin G resistant; methicillin susceptible
***Penicillin G and methicillin resistant In Table VI are summarized the results of agar-dilution tests wherein A-7413 factor A was tested against a variety of Streptococcus species. These tests employed trypticase-soy agar plus blood, $10^{-2}$ dilution of an overnight broth culture in 0.3% agar as an inoculum, giving approximately 5,000 bacteria per 7.5-mm of agar surface. Again, the results for vancomycin in the same test are reported for comparison. All strains tested are penicillin-G-resistant, Group-D-Streptococcus strains.

TABLE VI

| | MIC (mcg/ml) | |
|---|---|---|
| Streptococcus sp. | A-7413 factor A | Vancomycin |
| 238 | 0.25 | 2.0 |
| 282 | 0.25 | 2.0 |
| 9901 | 0.125 | 4.0 |
| 9913 | 0.25 | 2.0 |
| 9933 | 0.25 | 8.0 |
| 9960 | 0.25 | 4.0 |
| 12253P | 0.125 | 2.0 |
| Shrigley | 0.125 | 4.0 |
| Mitis | 0.125 | 4.0 |
| 55992 | 0.125 | 4.0 |
| 8043 | 0.125 | 4.0 |

In addition, A-7413 factor A is effective against *Neisseria meningitides*. In agar-dilution tests using trypticase-soy agar with 5% rabbit blood and 1% isovitalex, and a 1:100 dilution of an overnight broth culture as inoculum, A-7413 factor A had the following MIC values:

| N. meningitides Cultures | MIC (mcg/ml) |
|---|---|
| Os | 4.0 |
| Sabderlin | 2.0 |

The A-7413 compounds are relatively nontoxic. For example, the acute toxicity (LD$_{50}$) of A-7413 factor A, when administered by intraperitoneal injection to mice, was greater than 400 mg per kg.

Another advantageous property of the A-7413 complex and the A-7413 compounds is their ability to inhibit *Propionibacterium acnes*, a pathogen associated with acne. Representative A-7413 factor A was tested against *P. acnes* by the following procedure: Two-fold serial dilutions of test compounds are made in Actinomyces Broth (Baltimore Biological Laboratories). Each tube is inoculated with *P. acnes* to contain $10^4$ organisms per ml. After four-days incubation at 37° C., the tubes are observed. The lowest concentration of test compound which prevents growth is recorded as the minimal inhibitory concentration (MIC). The results of this test are summarized in Table VII.

TABLE VII

| P. acnes Culture | A-7413 Factor A MIC (mcg/ml) |
|---|---|
| ATCC 6919 | ≦1.25 |
| Clinical Isolate 1 | 2.50 |
| Clinical Isolate 2 | ≦1.25 |

The A-7413 complex and the A-7413 compounds also inhibit the growth of microorganisms which contribute to the development of periodontal disease. In Table VIII is summarized the activity of A-7413 factor A against representative oral bacteria. Activity was measured using the standard agar-dilution method and recording the minimal inhibitory concentrations (MIC) after an incubation of 48 hours.

TABLE VIII

| Organism | MIC (mcg/ml) |
|---|---|
| *Streptococcus mutans** | <0.25 |
| *Lactobacillus casei*** | ≲0.25 |
| *Neisseria perflava*** | 32.0 |

*tested on Mitis Salivarius agar with tellurite and thioglycolic acid added.
**tested on Brain Heart Infusion Agar.

In addition, in tests using an artificial S. mutans plaque systems, the A-7413 complex and A-7413 factor A inhibited plaque formation at levels as low as 0.01 percent.

Another important property of the A-7413 complex and of the A-7413 compounds is the ability to improve feed-utilization efficiency in animals. For example, the A-7413 antibiotics improve feed-utilization efficiency in ruminants which have a developed rumen function.

It is known that the efficiency of carbohydrate utilization in ruminants is increased by treatments which stimulate the animal's rumen flora to produce propionate compounds rather than acetate or butyrate compounds (for a more complete discussion see Church et. al. in "Digestive Physiology and Nutrition of Ruminants," Vol. 2, 1971, pp. 622 and 625).

The efficiency of feed use can be monitored by observing the production and concentration of propionate compounds in the rumen using the method described by Arthur P. Raun in U.S. Pat. No. 3,794,732 (see especially Example 5). Table IX shows the ratio of volatile-fatty-acid (VFA) concentrations in A-7413-factor-A-treated flasks to concentrations in control flasks in this test.

TABLE IX

| A-7413 factor A (mcg/ml) | Ratio of Treated to Control | | | |
|---|---|---|---|---|
| | Molar % propionate | Molar % acetate | Molar % butyrate | Total VFA mM/l. |
| 10.00 | 1.23 | 0.95 | 0.95 | 1.02 |
| 2.00 | 1.17 | 0.96 | 0.98 | 1.03 |
| 1.00 | 1.24 | 0.98 | 0.84 | 1.05 |
| 0.50 | 1.05 | 1.00 | 0.94 | 1.04 |
| 0.25 | 1.07 | 0.99 | 0.98 | 1.04 |

Carbohydrate-utilization efficiency is further measured by in vivo tests performed in animals which have had a fistula installed in their rumen, making it possible to withdraw specimens of the contents of the rumen.

The procedure used in testing cattle is also described in Raun's U.S. Pat. No. 3,794,732 (see Example 7).

Table X summarizes the results of such a test with A-7413 factor A wherein the mean percent increases in ruminal propionic acid concentration were averaged over six analyses in a 14-day treatment period.

TABLE X

| Treatment | % Propionic Acid Conc. | Increase over Control | Increase Relative to Control |
|---|---|---|---|
| Control | 20.8 | — | — |
| A-7413 factor A 100 mg/day | 25.4 | 4.6 | 22.1% |

In a similar test in sheep, using fistulated wethers, A-7413 complex also increased feed efficiency. The results of this test are summarized in Table XI.

TABLE XI

| Treatment | Molar % propionate | Increase over control | Increase Relative to control |
|---|---|---|---|
| Control | 24.2 | — | — |
| A-7413 complex 30 mg/day | 26.2 | 2.0 | 8.3% |

*Sampled 6 days over a 17-day treatment period

The A-7413 complex and A-7413 compounds are typically effective in increasing propionates and, thereby, the efficiency of feed utilization when administered to ruminants orally at rates of from about 0.05 mg/kg/day to about 10 mg/kg/day. Most beneficial results are achieved at a rate of about one mg/kg/day. A preferred method of administration of the A-7413 complex or A-7413 compound is by mixing it with the animals' feed; however, it can be administered in other ways, for example, tablets, drenches, boluses or capsules. Formulation of these various dosage forms can be accomplished by methods well known in the veterinary pharmaceutical art. Each individual dosage unit should contain a quantity of A-7413 compound or complex directly related to the proper daily dose for the animal to be treated.

An example of the useful growth-promoting property of the A-7413 complex and A-7413 compounds is found in poultry. In floor-pen tests using broiler chicks, A-7413 factor A added to the feed at a rate of 10 grams per ton of feed significantly improved weight gains and feed utilization efficiency. The A-7413 complex and A-7413 compounds are typically effective in promoting growth in poultry when administered with the animals' feed at rates of from about 0.5 to about 50 grams of A-7413 complex or compound per ton of animal feed. Most beneficial results are seen when the A-7413 complex or compound is administered at rates of from about 2.5 to about 10 grams of A-7413 complex or compound per ton of animal feed.

The culture solids, including medium constituents and mycelia, can be used without extraction or separation, but preferably after removal of water, as a source of the A-7413 complex. For example, after production of A-7413 antibiotic activity, the culture medium can be dried by lyophilization; the lyophilized medium can then be mixed directly into a feed premix.

In order to illustrate more fully the operation of this invention, the following examples are provided:

EXAMPLE 1

A. Shake-flask Fermentation of A-7413

A culture of Actinoplanes sp. NRRL 8122 was prepared by growing the organism or an 18-×150-mm agar slant having the following composition:

| Ingredient | Amount |
|---|---|
| Sucrose | 30 g |
| Peptone | 5 g |
| $K_2HPO_4$ | 1 g |
| Czapek's mineral mix solution* | 5 ml |
| Agar | 25 g |
| Deionized water | q.s. 1 liter |

*Czapek's Mineral Mix Solution
100 g KCl
100 g $MgSO_4 \cdot 7H_2O$
2 g $FeSO_4 \cdot 7H_2O$
q.s. to 1 liter with deionized water The slant medium was inoculated with Actinoplanes sp. NRRL 8122, and the inoculated slant was incubated at 25° C. for 10 to 14 days. The mature slant culture was covered with water, scraping with a sterile loop to loosen and fragment the mycelia and release the spores from the sporangia. One-half of the resulting suspension was used to inoculate 50 ml of a liquid vegetative medium having the following composition:

| Ingredient | Amount |
|---|---|
| Glucose | 10 g |
| Dextrin | 20 g |
| Soybean flour | 25 g |
| Yeast extract | 2.5 g |
| $CaCO_3$ | 2.5 g |
| Deionized water | q.s. 1000 ml |

The inoculated vegetative medium was incubated in a 250-ml Erlenmeyer flask at 25° C. for 72 hours on a shaker rotating through an arc two inches in diameter at 250 RPM.

This incubated vegetative medium may be used directly to inoculate the second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution having the following composition:

| Ingredient | Amount |
| --- | --- |
| Glycerol | 20% |
| Lactose | 10% |
| Deionized water | 70% |

The prepared suspensions are stored in the vapor phase of liquid nitrogen.

A stored suspension (1 ml) thus prepared was used to inoculate 50 ml of a first-stage vegetative medium having the same composition earlier described for the vegetative medium. The inoculated first-stage vegetative medium was incubated in a 250-ml wide-mouth Erlenmeyer flask at 25° C. for 72 hours on a shaker rotating through an arc two inches in diameter at 250 RPM.

B. Tank Fermentation of A-7413

In order to provide a larger volume of inoculum, 40 ml of the above-described incubated vegetative medium was used to inoculate 400 ml of a second-stage vegetative medium having the same composition as that of the first-stage vegetative medium. This inoculated second-stage vegetative medium, in a 2-liter flask, was incubated at 25° C. for about 48 hours on a shaker rotating through an arc two inches in diameter at 250 RPM.

One liter of the second-stage vegetative inoculum thus prepared was used to inoculate 100 liters of sterile production medium of the following composition:

| Ingredient | Amount |
| --- | --- |
| Soybean flour | 35 g |
| Corn oil | 40 g |
| $MgSO_4 \cdot 7H_2O$ | 2 g |
| $CaCO_3$ | 2 g |
| $FeCl_2 \cdot 4H_2O$ | 0.06 g |
| Deionized water | q.s. 1 liter |

After sterilization by heating at 120° C. for 30 minutes, the pH of the medium was 7.0. The inoculated production medium, in a 165-liter fermentation tank, was allowed to ferment for about 7 days at a temperature of 25° C. The fermentation medium was aerated with sterile air at the rate of approximately 0.5 to 1.0 volume of air per volume of culture medium per minute. The medium was stirred with conventional agitators at 250 RPM.

EXAMPLE 2

The A-7413 antibiotics were produced as described in Example 1, but a slant medium having the following composition was used to provide spores or mycelium for the initial inoculum:

| Ingredient | Amount |
| --- | --- |
| $Na_2S_2O_3$ | 0.5 g |
| Yeast extract | 2.0 g |
| $CaCO_3$ | 3.0 g |
| Vegetable juice* | 200 ml |
| Deionized water | 800 ml |
| pH adjusted to 7.2 by the addition of dilute sodium hydroxide | |

*V-8 Juice, Campbell Soup Company, Camden, N.J. 08101, U.S.A.

EXAMPLE 3

The A-7413 antibiotics were produced as described in Example 1, but using a vegetative medium and a second-stage vegetative medium of the following composition:

| Ingredient | Amount |
| --- | --- |
| Glucose | 10.0 g |
| Dextrin | 20.0 g |
| Soybean flour | 15.0 g |
| Yeast extract | 2.5 g |
| Soybean oil (refined) | 5.0 g |
| $CaCO_3$ | 2.5 g |
| Deionized water | q.s. 1 liter |

EXAMPLE 4

Separation of the A-7413 Complex

Whole fermentation broth (200 liters), prepared as described in Example 1, was made acidic (pH 3.5) by the addition of dilute sulfuric acid. The resulting acidic broth was filtered using a filter aid (Hyflo Super-cel, a diatomaceous earth, Johns-Manville Products Crop.). Methanol (100 liters) was added to the separated mucelial cake; this methanol suspension was stirred for 30 min. and then was separated by filtration. Methanol (100 liters) was again added to the separated mycelial cake, again stirring for 30 min. and separating by filtration. The two methanol extracts were concentrated under vacuum, removing the methanol to give an aqueous concentrate (10.5 liters). This aqueous concentrate was cooled (5° C.) for 24 hours. The oily upper layer which formed was separated and discarded. The aqueous lower layer (2 liters) was adjusted to pH 4.3 by the addition of dilute sulfuric acid. The resulting solution was extracted twice with one-half volumes of a chloroform:methanol (4:1) solution. These two extracts were combined and evaporated to dryness under vacuum. The residue thus obtained was dissolved in chloroform (150 ml); this solution was added to n-pentane (1500 ml). The resulting precipitate was separated by centrifugation and was dried under vacuum to give 15.8 g of the A-7413 complex as a tan powder.

EXAMPLE 5

Separation of the A-7413 Factors

A-7413 complex (26.4 g), obtained as described in Example 4, was dissolved in 200 ml of a chloroform:methanol (19:1) solution. The resulting solution was applied to a 5.8-×94.0-cm column of silica gel (Matheson, Grade 62, equilibrated with 5% water), prepared in chloroform:methanol (19:1). The column was developed using chloroform:methanol (19:1), collecting 150-ml fractions. Elution of the column was monitored by assaying fractions against *Staphylococcus aureus, Bacillus subtilis,* and *Sarcina lutea* and by thin-layer chromatography bioautography, using *S. lutea* as the detecting organism. Fractions were combined according to factor content and activity exhibited. The combined fractions were each evaporated to dryness under vacuum. Each of the residues thus obtained was dissolved in chloroform (50 ml); each chloroform solution was added to n-pentane (500 ml) to precipitate the desired factor. The results of the column were as follows:

| Factor Obtained | Fractions | Yield | Approximate Purity |
| --- | --- | --- | --- |
| A | 18–23 | 10.153 g | pure |
| A | 24–30 | 597.6 mg | 60% |
| B | 31–43 | 278.8 mg | 80% |

| Factor Obtained | Fractions | Yield | Approximate Purity |
|---|---|---|---|
| C | 49–56 | 218.4 mg | 60% |

The factors which were impure were subjected to further chromatography on silica gel columns, using the above-described procedure, to obtain purified factors B and C and an additional amount of purified factor A.

EXAMPLE 6

Crystallization of A-7413 Factor A

Purified factor A (1 g), obtained as described in Example 5, was dissolved in chloroform (10 ml). Absolute ethanol (10 ml; absolute ethanol contains 0.5% benzene) was added. The resulting solution was allowed to stand for two hours at room temperature and then was cooled to 5° C. overnight. The crystals which formed were separated by centrifugation, washed with ethanol and dried to give 513 mg of crystalline A-7413 factor A.

A-7413 factor A crystallized in a similar manner using the following solvents:
chloroform:sec-butanol
chloroform:n-propanol
chloroform:isopropanol
dimethylformamide:acetone
acetone:ethanol
aqueous ethanol

EXAMPLE 7

A-7413 Factor A Ammonium Salt

A-7413 factor A (200 mg), prepared as described in Example 6, was added to 0.01 N ammonium hydroxide (10 ml). This suspension was stirred for 20 minutes, using a Virtis blender. The insoluble material was then separated by centrifugation and was discarded. The supernatant solution was freeze dried to give 158.7 mg of A-7413 factor A ammonium salt as a yellow, water-soluble powder.

EXAMPLE 8

A-7413 Factor A Potassium Salt

A-7413 factor A (3 g), prepared as described in Example 6, was suspended in water (150 ml). The pH of the resulting suspension was 4.3 and was adjusted to ph 9.45 by the addition of 0.05 N potassium hydroxide (41 ml). This solution was stirred, using a blender, for 30 minutes. The insoluble material was then separated by centrifugation. The supernatant solution was freeze-dried to give 2.61 g of A-7413 factor A potassium salt as a yellow, water-soluble powder.

The potassium salt was further purified and crystallized by dissolving this powder (200 mg) in methanol (8 ml), centrifuging off insoluble impurities, adding diethyl ether to the separated supernatant solution and cooling (5° C.) for three days. The crystals which formed were separated by centrifugation and were dried to give 141.8 mg of crystalline A-7413 factor A potassium salt.

EXAMPLE 9

A-7413 Factor A Calcium Salt

A-7413 factor A (200 mg), prepared as described in Example 6, was dissolved in methanol (20 ml), and 0.1 N calcium hydroxide was slowly added to the methanol solution with stirring until the solution had a pH of 9.1. Diethyl ether (6 volumes) was added to the resulting solution to precipitate the salt. The precipitate was separated by centrifugation and was dried to give 80.1 mg of A-7413 factor A calcium salt. The product contained 1.81% calcium when analyzed by atomic-absorption analysis.

EXAMPLE 10

A-7413 Factor A Triethylamine Salt

A-7413 factor A (200 mg) was treated according to the method of Example 7, but using 0.01 N triethylamine, to give 122.2 mg of the triethylammonium salt of A-7413 factor A.

EXAMPLE 11

A-7413 Factor A Disodium Salt

A-7413 factor A (300 mg) was treated according to the method of Example 7, but using 0.01 N sodium hydroxide (30 ml), to give 260 mg of the disodium salt of A-7413 factor A as a yellow, water-soluble compound (2.67% Na by atomic-absorption analysis).

EXAMPLE 12

A-7413 Factor A Monosodium Salt

A-7413 factor A (200 mg) was treated according to the method of Example 9, but using 0.1 N sodium hydroxide to adjust the pH of the solution to pH 8.6, to give 151.6 mg of the monosodium salt of A-7413 factor A as a water-soluble compound (1.43% Na by atomic-absorption analysis).

EXAMPLES 13–18

A-7413 factor B disodium salt, prepared according to the method of Example 8, but using A-7413 factor B and 0.01 N sodium hydroxide.

A-7413 factor B ammonium salt, prepared according to the method of Example 7, but using A-7413 factor B.

A-7413 factor B barium salt, prepared according to the method of Example 9, but using A-7413 factor B and 0.1 N barium hydroxide.

A-7413 factor C monosodium salt, prepared according to the method of Example 9, but using A-7413 factor C and 0.1 N sodium hydroxide.

A-7413 factor C isopropylamine salt, prepared according to the method of Example 10, but using A-7413 factor C and 0.01 N isopropylamine.

A-7413 factor C magnesium salt, prepared according to the method of Example 9, but using A-7413 factor C and 0.1 magnesium hydroxide.

EXAMPLE 19

A-7413 Factor A Acetyl Ester Derivative

A-7413 factor A (500 mg) was dissolved in dimethyl sulfoxide (20 ml). Acetic anhydride (8 ml) was added to this solution, and the mixture was allowed to stand at room temperature for 22 hours. The mixture was concentrated under vacuum to a volume of about 15 ml. Methanol (15 ml) was added to the concentrate, and the resulting mixture was added to diethyl ether (240 ml). The precipitate which formed was separated by filtration and dried under vacuum to give 216 mg of the acetyl ester derivative of A-7413 factor A.

Figure 5:
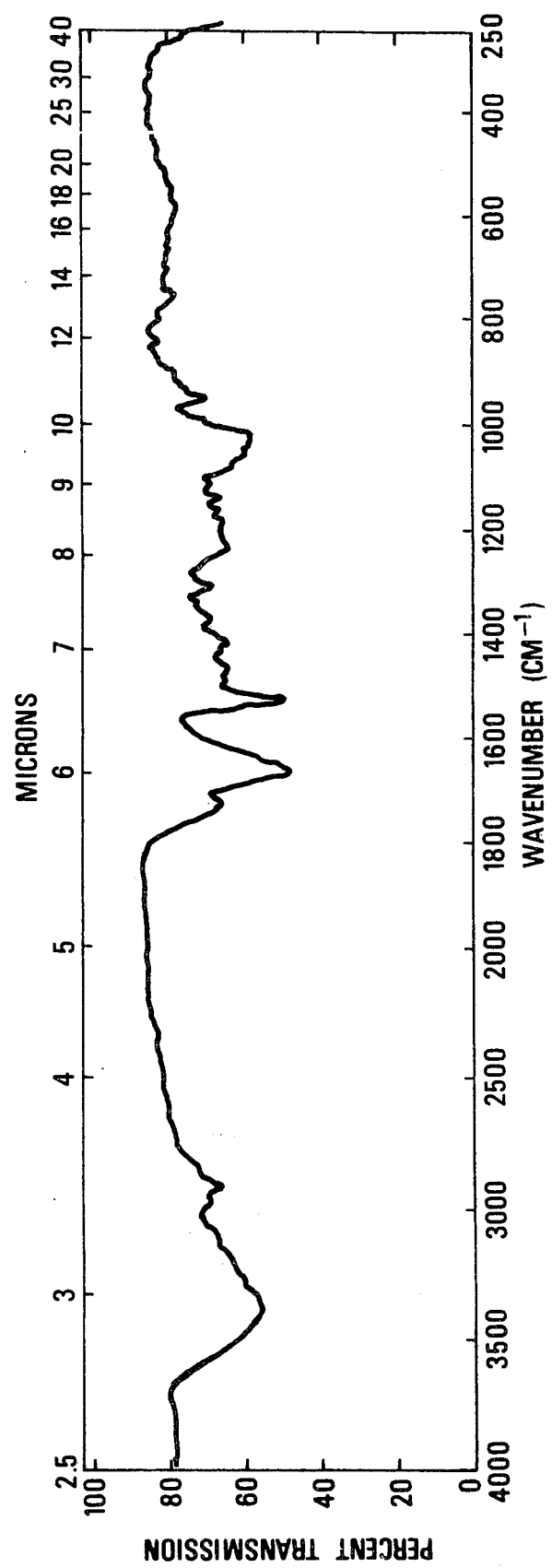

The infrared absorption spectrum of A-7413 factor A acetyl-ester derivative is shown in FIG. 5 of the accompanying drawings. The following absorption maxima are observed: 3450 (shoulder), 3380, 3100 (shoulder), 2980, 2920, 1730, 1668, 1530, 1470, 1418, 1375, 1312, 1242, 1190, 1165, 1140, 1118, 1075 (shoulder), 1055, 1030, 950, 840, 800 and 750 wavenumbers ($cm^{-1}$).

EXAMPLE 20

A-7413 Factor A Triacetyl Ester Derivative

A-7413 factor A (500 mg) was dissolved in pyridine (20 ml). Acetic anhydride (8 ml) was added to this solution, and the mixture was allowed to stand at room temperature for 22 hours. The mixture was then evaporated to dryness under vacuum. The residue was dissolved in chloroform (4 ml), and this solution was added to n-pentane (60 ml). The precipitate which formed was separated by centrifugation and dried under vacuum to give 421 mg of the acetyl ester derivative of A-7413 factor A.

Figure 6:
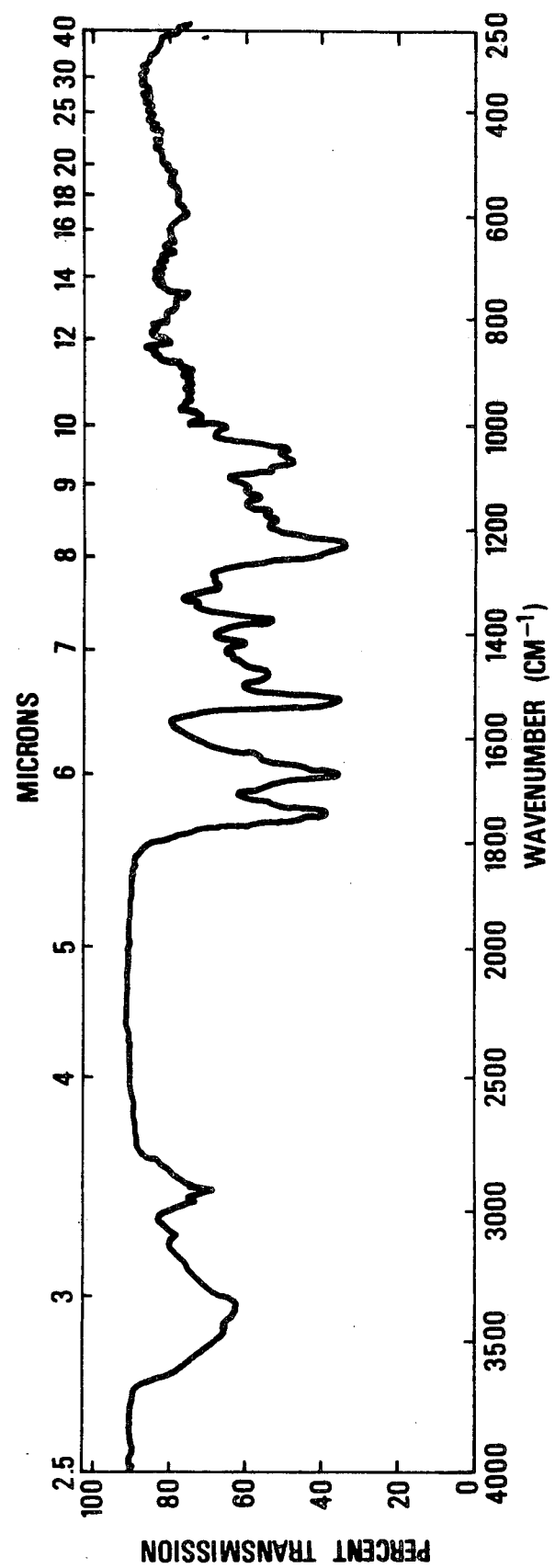

The infrared absorption spectrum of A-7413 factor A triacetyl-ester derivative is shown in FIG. 6 of the accompanying drawings. The following absorption maxima are observed: 3442 (shoulder), 3380, 3110, 2978, 2930, 2840 (shoulder), 1745, 1670, 1530, 1480, 1420, 1372, 1342, 1313, 1228, 1180, 1165, 1138, 1118, 1070, 1045, 1005, 985, 838 and 750 wavenumbers (cm$^{-1}$).

The nuclear-magnetic-resonance spectrum of A-7413 factor A triacetyl-ester derivative indicates the presence of acetyl methyl groups at 2.09 and 2.14 ppm, indicating the addition of at least three acetyl groups to A-7413 factor A.

EXAMPLES 21–25

A-7413 factor A propionyl ester derivative, prepared according to the method of Example 20, but using propionic anhydride.

A-7413 factor B n-butyryl ester derivative, prepared according to the method of Example 20, but using A-7413 factor B and n-butyric anhydride.

A-7413 factor C n-valeryl ester derivative, prepared according to the method of Example 20, but using A-7413 factor C and n-valeric anhydride.

A-7413 factor A succinyl ester derivative, prepared according to the method of Example 20, but using succinic anhydride.

A-7413 factor B formyl ester derivative, prepared according to the method of Example 20, but using acetic formic anhydride.

EXAMPLE 26

A-7413 Factor A Methyl Ester

A-7413 factor A (100 mg) was dissolved in a solution of methanol (5 ml) and chloroform (0.6 ml). An ethereal solution of diazomethane (4 ml) was added to the A-7413-factor-A solution. The resulting solution was stirred for 30 minutes and then was allowed to stand at room temperature for 4.5 hours. This solution was evaporated to dryness under vacuum. The residue obtained was dissolved in methanol (4 ml), and this solution was evaporated to dryness under vacuum. The residue obtained was dissolved in chloroform (3 ml), and the chloroform solution was added to n-pentane (30 ml). The precipitate which formed was separated by centrifugation and dried to give 87 mg of A-7413 methyl ester.

Figure 4:
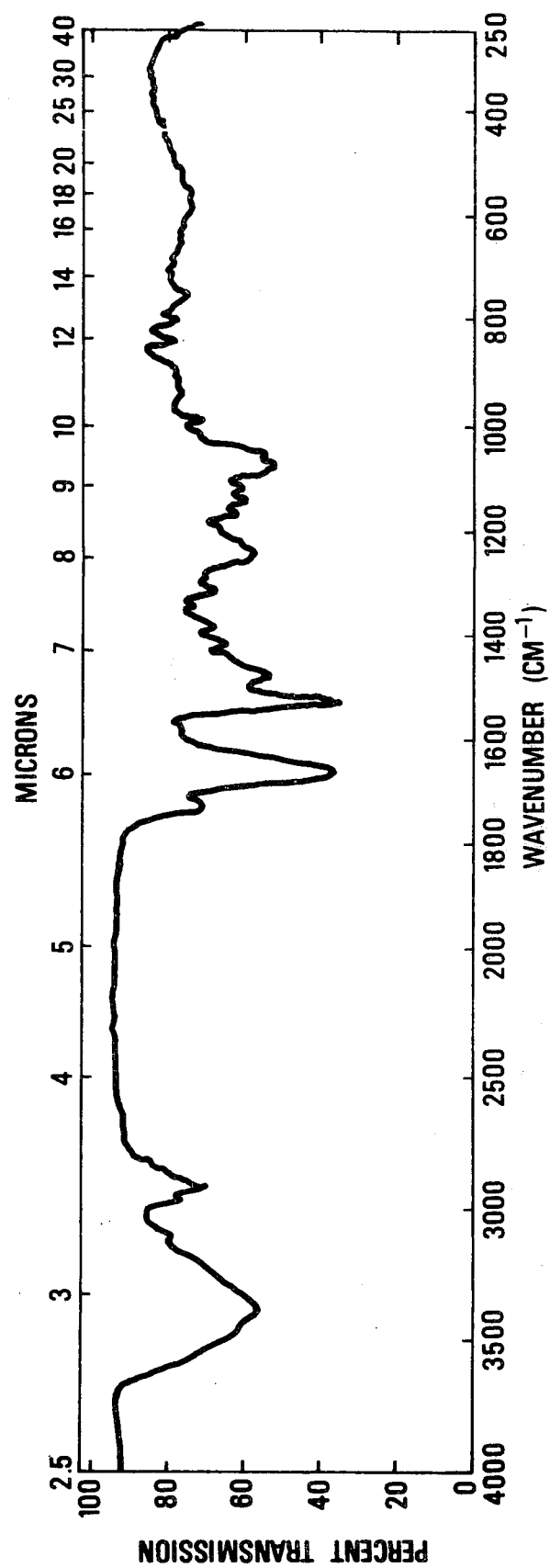

The infrared absorption spectrum of A-7413 factor A methyl ester is shown in FIG. 4 of the accompanying drawings. The following absorption maxima are observed: 3460 (shoulder), 3390, 3100, 2970 (shoulder), 2925, 1732, 1665, 1535, 1480, 1455 (shoulder), 1420, 1382, 1342, 1315, 1245, 1220 (shoulder), 1200 (shoulder), 1168, 1143, 1115, 1075, 1050, 985, 938, 840, 800 and 750 wavenumbers (cm$^{-1}$).

EXAMPLES 27–29

A-7413 factor B ethyl ester, prepared according to the method of Example 26, but using A-7413 factor B and diazoethane.

A-7413 factor C 2-propyl ester, prepared according to the method of Example 26, but using A-7413 factor C and diazo-2-propane.

A-7413 factor A n-butyl ester, prepared by reaction of A-7413 factor A with n-butanol by standard procedures, using dicyclohexylcarbodiimide as a dehydrating agent.

EXAMPLE 30

A-7413 Factor A Bis(Mercaptoacetic Acid) Derivative

A-7413 factor A (free acid; 200 mg) was dissolved in N,N-dimethylformamide (2.8 ml). Mercaptoacetic acid (200 mg) was added to this solution. The resulting solution was saturated with nitrogen by bubbling the gas through the solution for 30 minutes, and then was allowed to stand at room temperature for 20 hours. The solution was concentrated to a small volume; the concentrated solution was added to diethyl ether (25 volumes). The precipitate which formed was separated by filtration and dried to give 179 mg of the bis(mercaptoacetic acid)derivative of A-7413 factor A.

Figure 7:
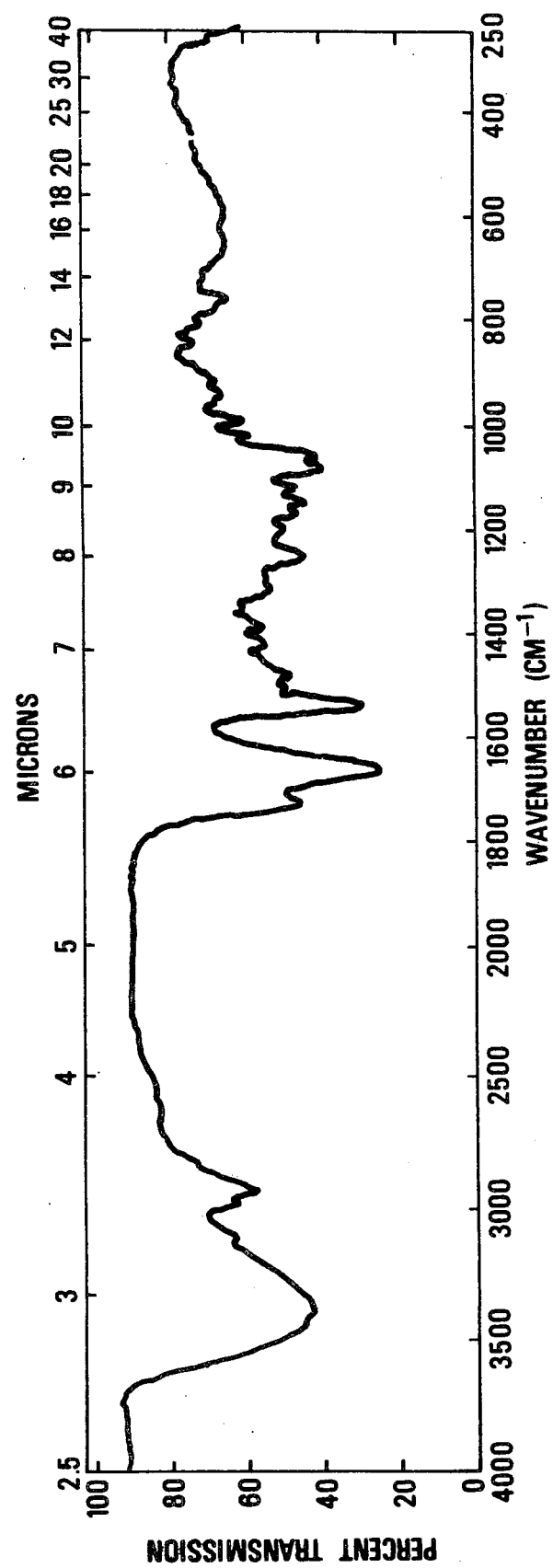

The infrared absorption spectrum of A-7413 factor A bis(mercaptoacetic acid)derivative in KBr disc is shown in FIG. 7 of the accompanying drawings. The following absorption maxima are observed: 3440 (shoulder), 3380, 3110, 2970, 2930, 2830 (shoulder), 1720, 1655, 1535, 1500, 1478, 1420, 1382, 1345, 1312, 1248, 1198, 1162, 1142, 1110, 1078, 1050, 1012, 985, 935, 908, 838, 800 and 752 wavenumbers (cm$^{-1}$).

EXAMPLES 31–35

A-7413 factor B bis(2-mercaptopropionic acid)-derivative, prepared according to the method of Example 30, but using A-7413 factor B and 2-mercaptopropionic acid.

A-7413 factor C bis(3-mercaptopropionic acid)-derivative, prepared according to the method Example 30, but using A-7413 factor C and 3-mercaptopropionic acid.

A-7413 factor A bis(mercaptosuccinic acid)derivative, prepared according to the method of Example 30, but using mercaptosuccinic acid.

A-7413 factor A mono-mercaptosuccinic acid derivative, prepared according to the method of Example 33, but allowing the solution to stand for only 6 hours.

A-7413 factor A L-cysteine derivative, prepared according to the method of Example 30, but using L-cysteine and purifying the product by chromatography.

We claim:

1. A method of increasing feed-utilization efficiency in ruminant animals which comprises orally administering to said animals an effective propionate-increasing amount of a member selected from a group consisting of (1) A-7413 complex produced by cultivating Actinoplanes sp. NRRL 8122 in a culture medium containing assimilable sources of carbohydrate, nitrogen and inorganic salts under submerged aerobic fermentation conditions until a substantial amount of antibiotic activity is produced; (2) A-7413 factor A which is a white to light-yellow crystalline material when crystallized from ethanol; which is soluble in methanol, chloroform, dimethylformamide, dichloroethane and dimethyl sulfoxide; is slightly soluble in ethanol and aqueous ethanol; but is insoluble in acetone, benzene, carbon tetrachloride, dichloromethane, methyl isobutyl ketone, ethyl acetate, diethyl ether and water; which melts with decomposition at about 205°–212° C. and which has:

(A) an apparent molecular weight of approximately 1308, as determined by titration;

(B) an approximate elemental composition of 51.92 percent carbon, 5.25 percent hydrogen, 9.85 percent nitrogen, 22.63 percent oxygen, and 9.66 percent sulfur;

(C) a proposed approximate empirical formula of $C_{72}H_{87}N_{12}O_{23}S_5$;

(D) a specific rotation, $[\alpha]_D^{25}$, of $+54.5°$ (c 2.0, $CHCl_3$);

(E) an infrared absorption spectrum in KBr disc with the following observable absorption maxima: 2.93 (shoulder), 2.98 (medium), 3.24 (weak), 3.38 (shoulder), 3.44 (medium), 3.53 (weak), 5.78 (weak), 6.03 (strong), 6.56 (strong), 6.79 (medium), 7.08 (medium), 7.27 (weak), 7.49 (weak), 7.65 (weak), 8.08 (medium), 8.41 (weak), 8.62 (weak), 8.81 (medium), 9.03 (weak), 9.35 (medium), 9.60 (medium), 9.92 (weak), 10.20 (weak), 12.05 (weak), 12.66 (weak), and 13.51 (weak) microns;

(F) an ultraviolet absorption spectrum with the following absorption maxima:
(a) in neutral, 95% aqueous ethanol:
215 nm ($E_{1cm}^{1\%}=485$);
260 nm (shoulder; $E_{1cm}^{1\%}=240$);
300 nm (shoulder; $E_{1cm}^{1\%}=170$);
358 nm (shoulder; $E_{1cm}^{1\%}=112.5$);
(b) in acidic ethanol:
217 nm ($E_{1cm}^{1\%}=440$);
265 nm ($E_{1cm}^{1\%}=227.5$);
293 nm ($E_{1cm}^{1\%}=210$);
358 nm ($E_{1cm}^{1\%}=95$);
(c) in basic methanol:
278 nm (shoulder; $E_{1cm}^{1\%}=255$);
408 nm ($E_{1cm}^{1\%}=80$);

(G) a titratable group with a $pK_a$ value of 7.9 in 80% aqueous dimethylformamide;

(H) an amino-acid analysis, after acidic hydrolysis, which indicates the presence of ammonia, glycine, threonine, aspartic acid, and an as-yet-unidentified amino acid;

(I) a characteristic X-ray powder diffraction pattern ($Cu^{++}$ radiation, 1.54505 λ, nickel filter) having the following interplanar spacings in angstroms (d):

| d | Relative Intensity |
|---|---|
| 12.44 | 100 |
| 10.77 | 70 |
| 7.96 | 100 |
| 5.71 | 50 |
| 5.09 | 80 |
| 4.53 | 100 |
| 4.25 | 80 |
| 3.88 | 80 |
| 3.61 | 10 |
| 3.44 | 10 |
| 3.03 | 5 |

(J) the following $R_f$ values in the paper-chromatographic systems indicated below, using *Bacillus subtilis* ATCC 6633 as a detection organism:

| $R_f$ Value | Solvent System |
|---|---|
| 0.57 | Butanol sat. with water |
| 0.49 | Methyl isobutyl ketone: butanol:water (25:21:4) |
| 0.62 | Metanol:water (1:1) |
| 0.30 | Water:methanol:acetone (12:3:1); adjusted to pH 10.5 with $NH_4OH$ and then lowered to pH 7.5 with $H_3PO_4$ |
| 0.71 | Methanol:0.1 N HCl (3:1) |

(K) the following $R_f$ values in the silica-gel thin-layer-chromatographic systems indicated below, using *Bacillus subtilis* as a detection organism:

| $R_f$ Value | Solvent System |
|---|---|
| 0.26 | Chloroform:methanol (9:1) |
| 0.23 | Acetonitrile: water (9:1) |

(L) an acid function capable of forming salts and ester derivatives;

(M) at least one hydroxy group capable of esterification; and (N) the ability to form derivatives with thiol carboxylic acids;

(3) A-7413 factor B which is a white to light-yellow amorphous material which melts above 300° C. and which is soluble in methanol, chloroform, dimethylformamide, dichloroethane and dimethyl sulfoxide; is slightly soluble in ethanol and aqueous ethanol; but is insoluble in acetone, benzene, carbon tetrachloride, dichloromethane, methyl isobutyl ketone, ethyl acetate, diethyl ether and water; and which has:

(A) an approximate elemental composition of 66.34 percent carbon, 8.73 percent hydrogen, 2.98 percent nitrogen, 19.39 percent oxygen, and 2.83 percent sulfur;

(B) a specific rotation, $[\alpha]_D^{RT}$, of $-26.2°$ (c 7.5, DMSO);

(C) an infrared absorption spectrum in KBr disc with the following observable absorption maxima: 2.97 (strong), 3.38 (strong), 3.42 (strong), 3.50 (strong), 5.78 (shoulder), 5.99 (medium), 6.50 (medium), 6.80 (medium), 6.90 (shoulder), 7.00 (shoulder), 7.22 (medium), 7.27 (shoulder), 7.42 (weak), 7.58 (weak), 7.78 (shoulder), 7.97 (medium), 8.33 (shoulder), 8.53 (medium), 9.00 (shoulder), 9.26 (strong), 9.71 (strong), 11.11 (weak), 11.79 (weak), 12.35 (weak) and 13.25 (weak) microns;

(D) an ultraviolet absorption spectrum with the following absorption maxima:
(a) in neutral, 95% aqueous ethanol:
268 nm ($E_{1cm}^{1\%}=104.3$);
357 nm (shoulder; $E_{1cm}^{1\%}=30$);
(b) in acidic ethanol:
268 nm ($E_{1cm}^{1\%}=108.5$);
357 nm (shoulder; $E_{1cm}^{1\%}=35$);
(c) in basic ethanol:
268 nm (shoulder; $E_{1cm}^{1\%}=178.6$);

(E) an amino-acid analysis, after acidic hydrolysis, which indicates the presence of ammonia, glycine, threonine, aspartic acid, and an as-yet-unidentified amino acid;

(F) the following $R_f$ values in the paper-chromatographic systems indicated below, using *Bacillus subtilis* ATCC 6633 as a detection organism:

| $R_f$ Value | Solvent System |
| --- | --- |
| 0.46 | Butanol sat. with water |
| 0.33 | Methyl isobutyl ketone: butanol:water (25:21:4) |
| 0.58 | Methanol:water (1:1) |
| 0.26 | Water:methanol:acetone (12:3:1); adjusted to pH 10.5 with $NH_4OH$ and then lowered to pH 7.5 with $H_3PO_4$ |
| 0.71 | Methanol:0.1 N HCl (3:1) |

(G) the following $R_f$ values in the silica-gel thin-layer-chromatographic systems indicated below, using *Bacillus subtilis* as a detection organism:

| $R_5$ Value | Solvent System |
| --- | --- |
| 0.09 | Chloroform: methanol (9:1) |
| 0.03 | Acetonitrile:water (9:1) |

(H) an acid function capable of forming salts and ester derivatives;

(I) at least one hydroxyl group capable of esterification; and (J) the ability to form derivatives with thiol carboxylic acids;

(4) A-7413 factor C which is a white to light-yellow amorphous material which melts above 250° C. and which is soluble in methanol, chloroform, dimethylformamide, dichloroethane and dimethyl sulfoxide; is slightly soluble in ethanol and aqueous ethanol; but is insoluble in acetone, benzene, carbon tetrachloride, dichloromethane, methyl isobutyl ketone, ethyl acetate, diethyl ether and water; and which has:

(A) an approximate elemental composition of 69.38 percent carbon, 9.92 percent hydrogen, 2.34 percent nitrogen, 16.58 percent oxygen, and 1.73 percent sulfur;

(B) an infrared absorption spectrum in KBr disc with the following observable absorption maxima: 3.00 (medium), 3.38 (shoulder), 3.42 (strong), 3.51 (strong), 5.73 (medium), 6.02 (medium), 6.14 (shoulder), 6.52 (weak), 6.56 (weak), 6.77 (medium), 6.80 (shoulder), 6.97 (weak), 7.20 (weak), 8.25 (weak), 8.33 (weak), 8.40 (weak), 8.86 (weak), 9.39 (weak), 10.05 (weak), 10.53 (weak), 10.70 (weak), 11.77 (weak) and 13.66 (weak) microns;

(C) an ultraviolet absorption spectrum with the following absorption maxima:
(a) in neutral, 95% aqueous ethanol:
205 nm ($E_{1cm}^{1\%}=356$);
235 nm (shoulder; $E_{1cm}^{1\%}=180$);
260 nm (shoulder; $E_{1cm}^{1\%}=127$);
290 nm (shoulder; $E_{1cm}^{1\%}=104$);
(b) in acidic ethanol:
205 nm ($E_{1cm}^{1\%}=356$);
235 nm (shoulder; $E_{1cm}^{1\%}=180$);
260 nm (shoulder; $E_{1cm}^{1\%}=127$);
290 nm (shoulder; $E_{1cm}^{1\%}=103$);
355 nm (shoulder; $E_{1cm}^{1\%}=40$);
(c) in basic ethanol:
260 nm (shoulder; $E_{1cm}^{1\%}=268$);
325 nm (shoulder; $E_{1cm}^{1\%}=189$);

(D) an amino-acid analysis, after acidic hydrolysis, which indicates the presence of ammonia, glycine, threonine, aspartic acid, and phenylalanine;

(E) the following $R_f$ values in the paper-chromatographic systems indicated below, using *Bacillus subtilis* ATCC 6633 as a detection organism:

| $R_5$ Value | Solvent System |
| --- | --- |
| 0.82 | Butanol sat. with water |
| 0.90 | Methyl isobutyl ketone: butanol:water (25:21:4) |
| 0.31 | Methanol:water (1:1) |
| 0.06 | Water:methanol:acetone (12:3:1); adjusted to pH 10.5 with $NH_3OH$ and then lowered to pH 7.5 with $H_3PO_4$ |
| 0.42 | Methanol:0.1 N HCl (3:1) |

(F) the following $R_f$ values in the silica-gel thin-layer-chromatographic systems indicated below, using *Bacillus subtilis* as a detection organism:

| $R_f$ Value | Solvent System |
| --- | --- |
| 0.46 | Chloroform:methanol (9:1) |
| 0.42 | Acetonitrile:water (9:1) |

(G) an acid function capable of forming salts and ester derivatives;

(H) at least one hydroxyl group capable of esterification; and (I) the ability to form derivatives with thiol carboxylic acids;

(5) the methyl ester derivative of A-7413 factor A, which is soluble in the same solvents as is A-7413 factor A, which has an approximate empirical formula of $C_{73}H_{89}N_{12}O_{23}S_5$, an ultraviolet absorption spectrum and an amino-acid content as given for A-7413 factor A, and which has an infrared absorption spectrum as shown in FIG. 4 of the drawings; (6) the acetyl and triacetyl ester derivatives of A-7413 factor A, each of which is soluble in the same solvents as is A-7413 factor A, each of which has an ultraviolet absorption spectrum, an amino-acid content, and an electrometric titration as given for A-7413 factor A, the acetyl-ester derivative having an approximate empirical formula of $C_{74}H_{89}N_{12}O_{24}S_5$ and an infrared absorption spectrum as shown in FIG. 5 of the drawings and the triacetyl-ester derivative having an approximate empirical formula of $C_{78}H_{93}N_{12}O_{26}S_5$ and an infrared absorption spectrum as shown in FIG. 6 of the drawings; and (7) the physiologically acceptable salts of A-7413 factors A, B, and C; or (8) the physiologically acceptable salts of the acetyl and triacetyl ester derivatives of A-7413 factor A.

2. The method of claim 1 wherein the member is A-7413 complex.

3. The method of claim 1 wherein the member is A-7413 factor A.

4. The method of claim 1 wherein the member is a physiologically-acceptable salt of A-7413 factor A.

5. The method of claim 1 wherein the member is A-7413 factor B.

6. The method of claim 1 wherein the member is a physiologically-acceptable salt of A-7413 factor B.

7. The method of claim 1 wherein the member is A-7413 factor C.

8. The method of claim 1 wherein the member is a physiologically-acceptable salt of A-7413 factor C.

9. A method of increasing feed-utilization efficiency in ruminant animals which comprises orally administering to said animals an effective propionate-increasing amount of (1) the bis(mercaptoacetic acid) derivative of A-7413 factor A, said derivative having an infrared absorption spectrum as shown in FIG. 7 of the drawings and being prepared by reaction A-7413 factor A, which is defined in claim 1, with an equivalent amount by weight of mercaptoacetic acid in a nonaqueous solvent for about 20 hours; or (2) a physiologically acceptable salt thereof.

* * * * *

UNITED STATES PATENT AND TRADEMARK OFFICE
CERTIFICATE OF CORRECTION

PATENT NO. : 4,174,390
DATED : November 13, 1979
INVENTOR(S) : Robert L. Hamill and W. Max Stark It is certified that error appears in the above-identified patent and that said Letters Patent are hereby corrected as shown below:

Column 2, line 65, "NRRl" should read -- NRRL --.

Column 3, line 39, "(medium," should read -- (medium), --; line 44, "ethanol;" should read -- ethanol: --; line 54, "basic methanol" should read -- basic ethanol --.

Column 4, line 59, "asyet" should read -- as-yet --; line 64, "about" should read -- above --.

Column 10, line 66, "Baceteriol." should read -- Bacteriol. --.

Column 12, line 51, "systems" should read -- system --.

Column 16, line 21, "Crop." should read -- Corp. --; line 23, "mucelial" should read -- mycelial --.

Column 17, line 46, "ph" should read -- pH --.

Column 21, line 39, "basic methanol" should read -- basic ethanol --.

UNITED STATES PATENT AND TRADEMARK OFFICE
CERTIFICATE OF CORRECTION

PATENT NO. : 4,174,390

DATED : November 13, 1979

INVENTOR(S) : Robert L. Hamill and W. Max Stark

It is certified that error appears in the above-identified patent and that said Letters Patent are hereby corrected as shown below:

Column 22, line 7, "Metanol:water" should read -- Methanol:water --; line 26, "hydroxy" should read -- hydroxyl --.

Column 23, line 21, "$R_5$ Value" should read -- $R_f$ Value --.

Column 24, line 9, "$R_5$ Value" should read -- $R_f$ Value --; line 15, "$NH_3OH$" should read -- $NH_4OH$ --.

Column 26, line 1, "reaction" should read -- reacting --.

Signed and Sealed this

Thirteenth Day of January 1981

[SEAL]

Attest:

SIDNEY A. DIAMOND

Attesting Officer

Commissioner of Patents and Trademarks